(12) United States Patent
Sakai et al.

(10) Patent No.: US 9,585,544 B2
(45) Date of Patent: Mar. 7, 2017

(54) SCANNING ENDOSCOPE SYSTEM (71) Applicant: OLYMPUS CORPORATION, Tokyo (JP)

(72) Inventors: Yuji Sakai, Kodaira (JP); Yoshinari Okita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 317 days.

(21) Appl. No.: 14/311,639

(22) Filed: Jun. 23, 2014

(65) Prior Publication Data

US 2014/0354790 A1 Dec. 4, 2014

Related U.S. Application Data

(63) Continuation of application No. PCT/JP2013/080226, filed on Nov. 8, 2013.

(30) Foreign Application Priority Data

Dec. 4, 2012 (JP) ................... 2012-265538

(51) Int. Cl.
*A61B 1/00* (2006.01)
*A61B 1/07* (2006.01)
*G02B 26/10* (2006.01)

(52) U.S. Cl.
CPC ...... *A61B 1/00098* (2013.01); *A61B 1/00006* (2013.01); *A61B 1/00059* (2013.01);
(Continued)

(58) Field of Classification Search
CPC ............ A61B 1/00098; A61B 1/00006; A61B 1/00059
(Continued)

(56) References Cited

U.S. PATENT DOCUMENTS

2008/0165360 A1 7/2008 Johnston
2008/0208232 A1* 8/2008 Yamada ......... A61B 17/320068
606/169
(Continued)

FOREIGN PATENT DOCUMENTS

JP 2001-174744 A 6/2001
JP 2010-268972 A 12/2010
(Continued)

OTHER PUBLICATIONS

Extended Supplementary European Search Report dated May 4, 2016 in related European Application No. 13 86 0478.0.

*Primary Examiner* — Jeffery Williams
(74) *Attorney, Agent, or Firm* — Scully, Scott, Murphy & Presser. P.C.

(57) ABSTRACT

A scanning endoscope system includes a fiber, a first actuator that is provided laterally of the fiber to swing the fiber, a second actuator that is arranged at a position opposite to the first actuator with the fiber intervened in between to swing the fiber, and a driver unit that outputs, to the first actuator, a first drive signal having either a first waveform such that a minimum value of a voltage value, which varies periodically with a positive voltage value as a center, is not less than zero, or a second waveform such that a maximum value of a voltage value, which varies periodically with a negative voltage value as a center, is not more than zero, and configured to output, to the second actuator, a second drive signal having the same waveform as the first drive signal and different phase from the first drive signal.

10 Claims, 4 Drawing Sheets

(52) U.S. Cl.
CPC ............ *A61B 1/00172* (2013.01); *A61B 1/07* (2013.01); *G02B 26/103* (2013.01)

(58) Field of Classification Search
USPC .......................................................... 348/68
See application file for complete search history.

(56) References Cited

U.S. PATENT DOCUMENTS

| | | |
|---|---|---|
| 2008/0218824 A1 | 9/2008 | Johnston et al. |
| 2009/0028407 A1 | 1/2009 | Seibel et al. |
| 2009/0189485 A1* | 7/2009 | Iyoki ...................... B82Y 35/00 310/317 |
| 2009/0218641 A1* | 9/2009 | Melville ................ H01L 41/092 257/415 |
| 2010/0121146 A1* | 5/2010 | Sugimoto ............ A61B 1/0008 600/117 |

FOREIGN PATENT DOCUMENTS

| | | |
|---|---|---|
| JP | 2011-115252 A | 6/2011 |
| JP | 2012-152244 A | 8/2012 |

* cited by examiner

SCANNING ENDOSCOPE SYSTEM

CROSS REFERENCE TO RELATED APPLICATION

This application is a continuation application of PCT/JP2013/080226 filed on Nov. 8, 2013 and claims benefit of Japanese Application No. 2012-265538 filed in Japan on Dec. 4, 2012, the entire contents of which are incorporated herein by this reference.

BACKGROUND OF THE INVENTION

1. Field of the Invention

The present invention relates to a scanning endoscope system, and in particular to a scanning endoscope system that acquires an image by scanning an object.

2. Description of the Related Art

In respect to an endoscope in a medical field, there have been proposed various techniques for decreasing a diameter of an insertion portion to be inserted into a body cavity of a subject to be examined in order to reduce a burden on the subject. Further, as an example of such techniques, there are known a scanning endoscope that does not include a solid-state image pickup device at a portion corresponding to the above-mentioned insertion portion, and a system that is configured to include the scanning endoscope.

Specifically, the system including the scanning endoscope is configured such that the object is two-dimensionally scanned in a preset scanning pattern by swinging a distal end portion of an illumination fiber that guides illumination light emitted from a light source section, and return light from the object is received by a receiving fiber arranged around the illumination fiber, and an image of the object is generated based on the return light received by the receiving fiber. Then, there is known a scanning beam system disclosed in U.S. Patent Application Publication No. 2008/0218824, for example, which has a configuration similar to the configuration of such a system.

Incidentally, in the conventional scanning endoscope as described above, it is configured that the illumination fiber is swung by applying a voltage to an actuator formed by using a piezoelectric device which is subjected to polarization processing in advance.

Further, in U.S. Patent Application Publication No. 2008/0218824, there is disclosed a configuration in which an optical fiber corresponding to the above-mentioned illumination fiber is swung by applying an AC voltage in accordance with a drive signal having positive and negative amplitudes with "0" as a center.

SUMMARY OF THE INVENTION

A scanning endoscope system according to an aspect of the present invention includes: a fiber that conducts illumination light emitted from a light source; a first actuator that is provided laterally of the fiber, and expands and contracts in accordance with an applied voltage so as to swing the fiber; a second actuator that is arranged at a position opposite to the first actuator with the fiber intervened in between, and expands and contracts in accordance with an applied voltage so as to swing the fiber; and a drive-signal output section configured to output, to the first actuator, a first drive signal having either a first waveform such that a minimum value of a voltage value, which varies periodically with a first voltage value of a positive value as a center, is not less than zero, or a second waveform such that a maximum value of a voltage value, which varies periodically with a second voltage value of a negative value as a center, is not more than zero, and configured to output, to the second actuator, a second drive signal having the same waveform as the first drive signal and having a phase different from a phase of the first drive signal.

DETAILED DESCRIPTION OF THE PREFERRED EMBODIMENTS

Hereinafter, embodiments of the present invention will be described referring to the drawings.

Figure 1:
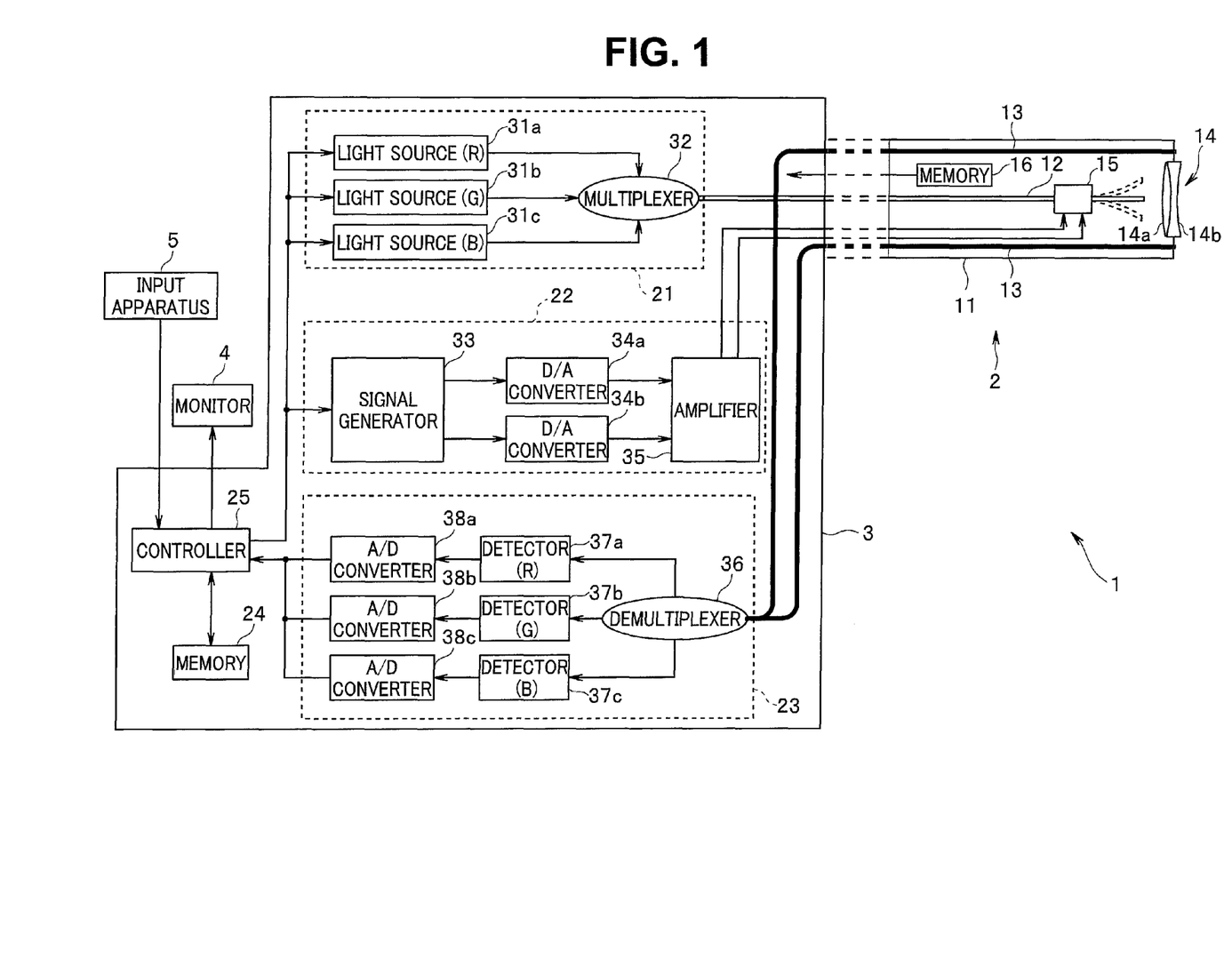
FIG. 1 is a diagram showing a configuration of a principal part of a scanning endoscope system according to an embodiment.

FIGS. 1-6 relate to the embodiments of the present invention. FIG. 1 is a diagram showing a configuration of a principal part of a scanning endoscope system according to the embodiment.

A scanning endoscope system 1 is configured to include a scanning endoscope 2 to be inserted into a body cavity of a subject to be examined, a main body apparatus 3 connected to the scanning endoscope 2, a monitor 4 connected to the main body apparatus 3, and an input device 5 capable of inputting and instructing information to the main body apparatus 3, as shown in FIG. 1, for example. Besides, the input device 5 is not limited to be configured as a device separate from the main body apparatus 3, as shown in FIG. 1, but may be configured as an interface integrated with the main body apparatus 3.

The scanning endoscope 2 is configured to include an insertion portion 11 formed to have an elongated shape and flexibility capable of being inserted into the body cavity of the subject. At a proximal end portion of the insertion portion 11, there is provided a connector or the like, which is not shown, for connecting the scanning endoscope 2 to the main body apparatus 3.

An illumination fiber 12 having a function of a light conducting portion that conducts illumination light supplied from a light source unit 21 of the main body apparatus 3 to a light condensing optical system 14, and a light receiving fiber 13 that receives return light from an object and conducts the light to a detection unit 23 of the main body apparatus 3 are inserted through a part from the proximal end portion to a distal end portion inside the insertion portion 11.

An end portion of the illumination fiber 12 that includes a light entering face is arranged at a multiplexer 32 provided inside the main body apparatus 3. Further, an end portion of the illumination fiber 12 that includes a light emitting face is arranged in the vicinity of a light entering face of a lens 14a provided at the distal end portion of the insertion portion 11 in a state where the end portion is not fixed by a fixing member or the like.

An end portion of the light receiving fiber 13 that includes a light entering face is arranged and fixed around a light emitting face of a lens 14b on a distal end face of the distal end portion of the insertion portion 11. Further, an end portion of the light receiving fiber 13 that includes a light emitting face is arranged at a demultiplexer 36 provided inside the main body apparatus 3.

The light condensing optical system 14 includes the lens 14a and the lens 14b, and is configured so as to condense the illumination light incident on the lens 14a through the illumination fiber 12 and emit the condensed illumination light toward the object from the lens 14b.

At an intermediate portion of the illumination fiber 12 on a side of the distal end portion of the insertion portion 11, there is provided an actuator unit 15 that performs driving on the basis of a drive signal outputted from a driver unit 22 of the main apparatus body 3.

Figure 2:
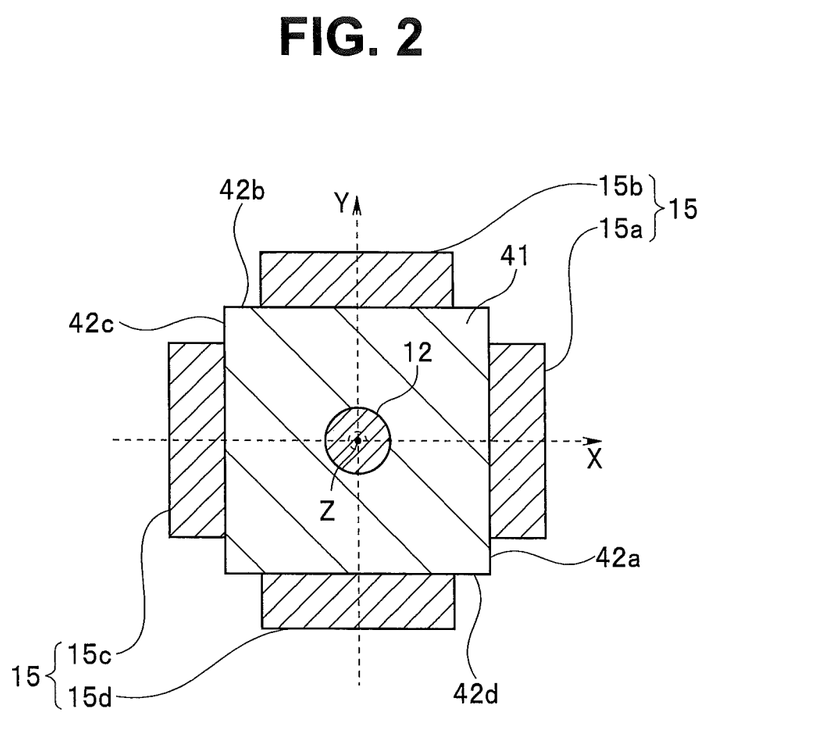
FIG. 2 is a sectional view for explaining a configuration of an actuator unit provided in a scanning endoscope.

On the other hand, the illumination fiber 12 and the actuator unit 15 are respectively arranged to have positional relation as shown in FIG. 2 on a cross section perpendicular to a longitudinal axis direction of the insertion portion 11. FIG. 2 is a sectional view for explaining a configuration of the actuator unit provided in the scanning endoscope.

As shown in FIG. 2, a ferrule 41 as a joining member is arranged between the illumination fiber 12 and the actuator unit 15. Specifically, the ferrule 41 is formed by zirconia (ceramic) or nickel or the like.

The ferrule 41 is formed into a quadrangular prism as shown in FIG. 2 and has side surfaces 42a and 42c perpendicular to an X-axis direction (right/left direction on the paper plane) and side surfaces 42b and 42d perpendicular to a Y-axis direction (up/down direction on the paper plane). Further, at a center of the ferrule 41, the illumination fiber 12 is fixedly arranged. It is noted that the ferrule 41 may be formed into another shape other than the quadrangular prism as long as the ferrule is a prism.

The actuator unit 15 includes an actuator 15a arranged along the side surface 42a, an actuator 15b arranged along the side surface 42b, an actuator 15c arranged along the side surface 42c and an actuator 15d arranged along the side surface 42d.

In other words, the actuator unit 15 having a function as a light scanning section is configured to include a pair of actuators 15a and 15c which are arranged at positions opposed to the Y-axis (or symmetrical with respect to the Y-axis) with the illumination fiber 12 intervened in between and arranged along the X-axis, and a pair of actuators 15b and 15d which are arranged at positions opposed to the X-axis (or symmetrical with respect to the X-axis) with the illumination fiber 12 intervened in between and arranged along the Y-axis.

It is configured that the actuators 15a, 15b, 15c and 15d are respectively driven in accordance with drive signals outputted from the driver unit 22.

The actuator 15a is formed by a piezoelectric device which is subjected to polarization processing in advance so that a polarization direction coincides with a negative direction of the X-axis (a direction from right to left on the paper plane), for example, and is configured to contract along a Z-axis (a direction normal to the paper plane) when a voltage of a positive value is applied (when a direction of an electric field generated in accordance with supply of the drive signal is a forward direction with respect to the polarization direction), and to expand along the Z-axis when a voltage of a negative value is applied (when the direction of the electric field generated in accordance with supply of the drive signal is a reverse direction with respect to the polarization direction) in accordance with the drive signal outputted from the driver unit 22.

The actuator 15b is formed by a piezoelectric device which is subjected to polarization processing in advance so that a polarization direction coincides with a negative direction of the Y-axis (a direction from up to down on the paper plane), for example, and is configured to contract along the Z-axis when a voltage of a positive value is applied and to expand along the Z-axis when a voltage of a negative value is applied, in accordance with the drive signal outputted from the driver unit 22.

The actuator 15c is formed by a piezoelectric device which is subjected to polarization processing in advance so that a polarization direction coincides with a positive direction of the X-axis (a direction from left to right on the paper plane), for example, and is configured to contract along the Z-axis when a voltage of a positive value is applied and to expand along the Z-axis when a voltage of a negative value is applied, in accordance with the drive signal outputted from the driver unit 22. That is, in the present embodiment, it is configured that the polarization direction of the piezoelectric device of the actuator 15a and the polarization direction of the piezoelectric device of the actuator 15c are opposite to each other.

The actuator 15d is formed by a piezoelectric device which is subjected to polarization processing in advance so that a polarization direction coincides with a positive direction of the Y-axis (a direction from down to up on the paper plane), for example, and is configured to contract along the Z-axis when a voltage of a positive value is applied and to expand along the Z-axis when a voltage of a negative value is applied, in accordance with the drive signal outputted from the driver unit 22. That is, in the present embodiment, it is configured that the polarization direction of the piezoelectric device of the actuator 15b and the polarization direction of the piezoelectric device of the actuator 15d are opposite to each other.

Besides, according to the present embodiment, it is not limited that the actuator unit 15 is configured by using the actuators 15a-15d having the polarization directions and the contracting/expanding directions as described above, but it may be configured that the actuator unit 15 is configured by using actuators 15a-15d having other polarization directions and contracting/expanding directions.

Inside the insertion portion 11, there is provided a memory 16 in which endoscope information including various pieces of information such as individual identification information of the scanning endoscope 2 is stored in advance. Further, the endoscope information stored in the memory 16 is read by a controller 25 of the main apparatus body 3 when the scanning endoscope 2 is connected with the main body apparatus 3.

On the other hand, the main body apparatus 3 is configured to include the light source unit 21, the driver unit 22, the detection unit 23, a memory 24 and the controller 25.

The light source unit 21 is configured to include a light source 31a, a light source 31b, a light source 31c and the multiplexer 32.

The light source 31a includes a laser source, for example, and is configured to emit light of a red wavelength band (hereinafter also referred to as "R-light") to the multiplexer 32 when it is turned on by control of the controller 25.

The light source 31b has a laser source, for example, and is configured to emit light of a green wavelength band (hereinafter also referred to as "G-light") to the multiplexer 32 when it is turned on by control of the controller 25.

The light source 31c has a laser source, for example, and is configured to emit light of a blue wavelength band (hereinafter also referred to as "B-light") to the multiplexer 32 when it is turned on by control of the controller 25.

The multiplexer 32 is configured to be able to multiplex the R-light emitted from the light source 31a, the G-light emitted from the light source 31b and the B-light emitted from the light source 31c and to supply multiplexed light to the light entering face of the illumination fiber 12.

The driver unit 22 has a function as a drive signal output section and is configured to include a signal generator 33, D/A converters 34a and 34b and an amplifier 35.

The signal generator 33 is configured to generate the drive signal for swing the end portion of the illumination fiber 12 including the light emitting face based on control of the controller 25 and output the generated signal to the D/A converters 34a and 34b.

The D/A converters 34a and 34b are each configured to convert a digital drive signal outputted from the signal generator 33 into an analog drive signal and output the converted signal to the amplifier 35.

The amplifier 35 is configured to amplify the drive signals outputted from the D/A converters 34a and 34b and output to the actuator unit 15.

On the other hand, the detection unit 23 is configured to include a demultiplexer 36, detectors 37a, 37b and 37c, and A/D converters 38a, 38b and 38c.

The demultiplexer 36 includes a dichroic mirror, etc. and is configured to split the return light emitted from the light emitting face of the receiving fiber 13 into light of respective color components of R (red), G (green) and B (blue) and emit the light to the detectors 37a, 37b and 37c.

The detector 37a is configured to detect intensity of the R-light outputted from the demultiplexer 36, generate an analog R-signal in accordance with the intensity of the detected R-light, and output the generated signal to the A/D converters 38a.

The detector 37b is configured to detect intensity of the G-light outputted from the demultiplexer 36, generate an analog G-signal in accordance with the intensity of the detected G-light, and output the generated signal to the A/D converters 38b.

The detector 37c is configured to detect intensity of the B-light outputted from the demultiplexer 36, generate an analog B-signal in accordance with the intensity of the detected B-light, and output the generated signal to the A/D converters 38c.

The A/D converters 38a is configured to convert the analog R-signal outputted from the detector 37a into a digital R-signal and output the converted signal to the controller 25.

The A/D converters 38b is configured to convert the analog G-signal outputted from the detector 37b into a digital G-signal and output the converted signal to the controller 25.

The A/D converters 38c is configured to convert the analog B-signal outputted from the detector 37c into a digital B-signal and output the converted signal to the controller 25.

In the memory 24, a control program for performing control of the main body apparatus 3 and so forth are stored in advance. Further, in the memory 24, the endoscope information read by the controller 25 of the main body apparatus 3 is stored.

The controller 25 includes a CPU, etc. and is configured to read the control program stored in the memory 24 and perform control of the light source unit 21 and the driver unit 22 based on the read control program. That is, the actuator unit 15 having a function as a light scanning section is capable of swinging the illumination fiber 12 so that an irradiation position of the illumination light which is irradiated to the object draws a locus according to a predetermined scanning pattern based on the drive signals outputted from the driver unit 22 under the control of the controller 25 as described above.

The controller 25 operates such that the endoscope information outputted from the memory 16 when the insertion portion 11 is connected to the main body apparatus 3 is stored in the memory 24.

The controller 25 is configured to generate an image based on the R-signal, the G-signal and the B-signal outputted from the detection unit 23 and display the generated image on the monitor 4.

Subsequently, an operation, etc. of the scanning endoscope system 1 having the configuration described above will be described.

When power is supplied to respective parts of the scanning endoscope system 1, the endoscope information stored in the memory 16 in the insertion portion 11 is read by the controller 25, and the read endoscope information is stored in the memory 24.

The controller 25, after storing the endoscope information read from the memory 16 in the memory 24, performs control of the light source unit 21 to switch the light sources 31a, 31b and 31c from off to on, and control of the driver unit 22 to output first and second drive signals, as described below, from the signal generator 33.

Figure 3:
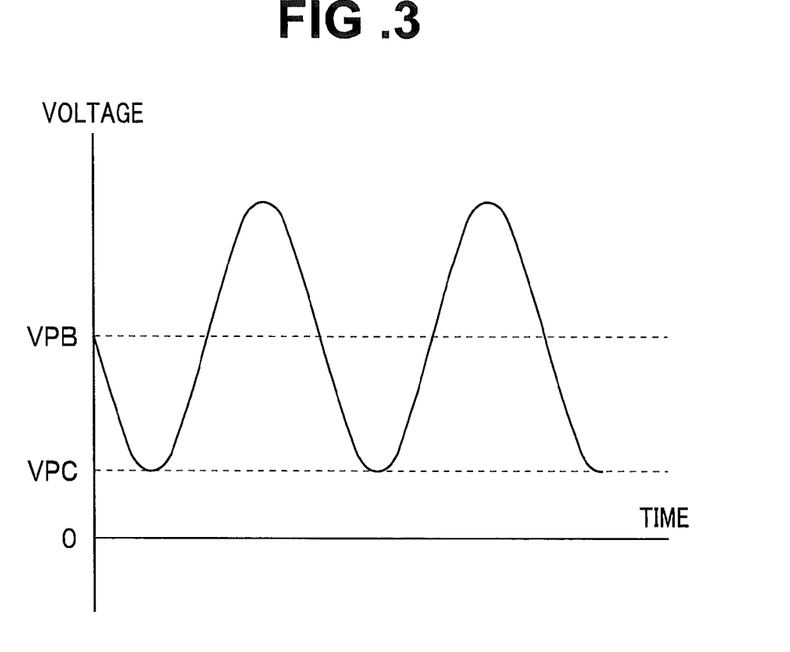
FIG. 3 is a diagram showing an example of a first drive signal used for driving the actuator unit provided in the scanning endoscope.

The signal generator 33 generates a first drive signal having a waveform and a phase as shown in FIG. 3, for example, as a drive signal for driving the actuators 15a and 15b on the basis of the control of the controller 25, and outputs the generated signal to the D/A converter 34a. FIG. 3 is a diagram showing an example of the first drive signal used in driving the actuator unit provided in the scanning endoscope.

Specifically, the signal generator 33 generates and outputs a first drive signal having a waveform such that a voltage value varies periodically with a voltage value VPB, which is a positive value, as a center and a minimum value VPC of the voltage value is not less than "0", and having an inverse phase with respect to a phase of a second signal of FIG. 4 (as described below) on the basis of control of the controller 25 (see FIG. 3).

Figure 4:
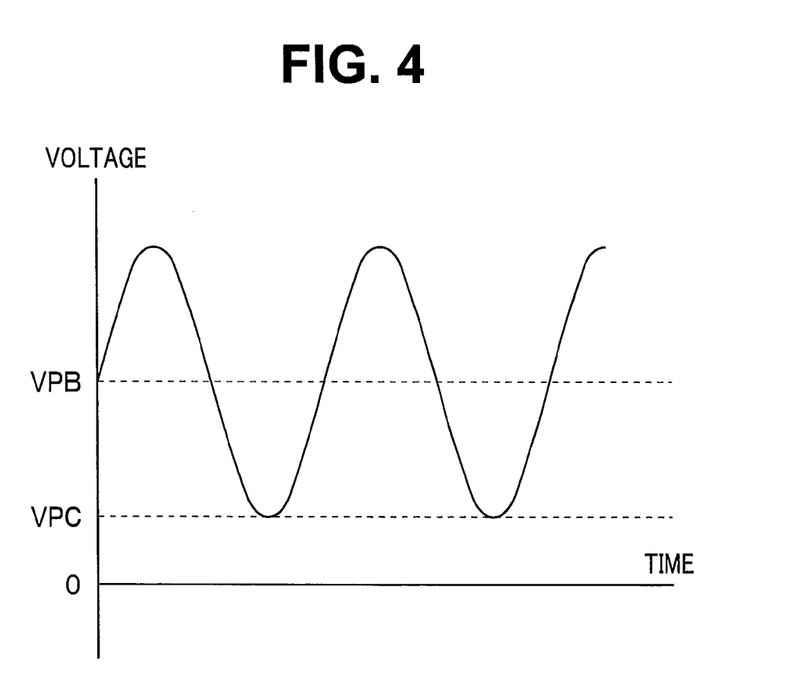
FIG. 4 is a diagram showing an example of a second drive signal used for driving the actuator unit provided in the scanning endoscope.

Further, the signal generator 33 generates a second drive signal having a waveform and a phase as shown in FIG. 4, for example, as a drive signal for driving the actuators 15c and 15d on the basis of the control of the controller 25, and outputs the generated signal to the D/A converter 34b. FIG. 4 is a diagram showing an example of the second drive signal used in driving the actuator unit provided in the scanning endoscope.

Specifically, the signal generator 33 generates and outputs the second drive signal having the same waveform as the first drive signal of FIG. 3 (in which the voltage value varies periodically with the positive voltage value VPB as the center and the minimum value VPC of the voltage value is not less than "0"), and having an inverse phase with respect to the phase of the first signal of FIG. 3, on the basis of control of the controller 25 (see FIG. 4).

It is noted that the above-mentioned voltage value VPB may be a fixed value which is set in advance or a variable value which is changeable in accordance with an operation of the input device 5 as long as the value VPB is the same in the first drive signal and the second drive signal, and the minimum value VPC of the voltage value is not less than "0".

On the other hand, the first drive signal of FIG. 3 generated by the signal generator 33 is outputted to the actuators 15a and 15b through the D/A converters 34a and the amplifier 35. Further, the second drive signal of FIG. 4 generated by the signal generator 33 is outputted to the actuators 15c and 15d through the D/A converter 34b and the amplifier 35.

Then, when an AC voltage in accordance with the first drive signal having the waveform and the phase as shown in FIG. 3 is applied to the actuator unit 15 (the actuators 15a and 15b), an electric field is generated in the forward direction (the negative direction of the X-axis) with respect to the polarization direction of the piezoelectric device constituting the actuator 15a, and an electric field is generated in the forward direction (the negative direction of the Y-axis) with respect to the polarization direction of the piezoelectric device constituting the actuator 15b. Further, when an AC voltage in accordance with the second drive signal having the waveform and the phase as shown in FIG. 4 is applied to the actuator unit 15 (the actuators 15c and 15d), an electric field is generated in the forward direction (the positive direction of the X-axis) with respect to the polarization direction of the piezoelectric device constituting the actuator 15c, and an electric field is generated in the forward direction (the positive direction of the Y-axis) with respect to the polarization direction of the piezoelectric device constituting the actuator 15d.

That is, the AC voltage in accordance with the first drive signal having the waveform and the phase as shown in FIG. 3 is applied to the actuators 15a and 15b, and the AC voltage in accordance with the second signal having the waveform and the phase as shown in FIG. 4 is applied to the actuators 15c and 15d, and thereby forces exerted to the ferrule 41 in accordance with the driving of the actuators 15a-15d can be balanced.

Incidentally, in a case where the illumination fiber 12 is swung according to a conventional method in which an AC voltage in accordance with a drive signal having positive and negative amplitudes with a voltage value "0" as a center is applied to the actuators 15a-15d, there arises necessity of configuring the main body apparatus 3 using an amplifier that amplifies both of the positive amplitude and the negative amplitude (as the amplifier 35) and is relatively expensive.

In contrast, according to the present embodiment, since the AC voltages in accordance with the drive signals each having the waveform in which the voltage value varies periodically with the positive voltage value VPB as the center and the minimum value VPC of the voltage value is not less than "0" are applied to the actuators 15a-15d, the main body apparatus 3 can be configured using an amplifier that amplifies only an amplitude of a positive value and is relatively inexpensive (as the amplifier 35). As a result, according to the present embodiment, it is possible to perform scanning of an object by the configuration of a relatively low cost in comparison with a conventional scanning endoscope system while maintaining the same function as the conventional system.

Figure 5:
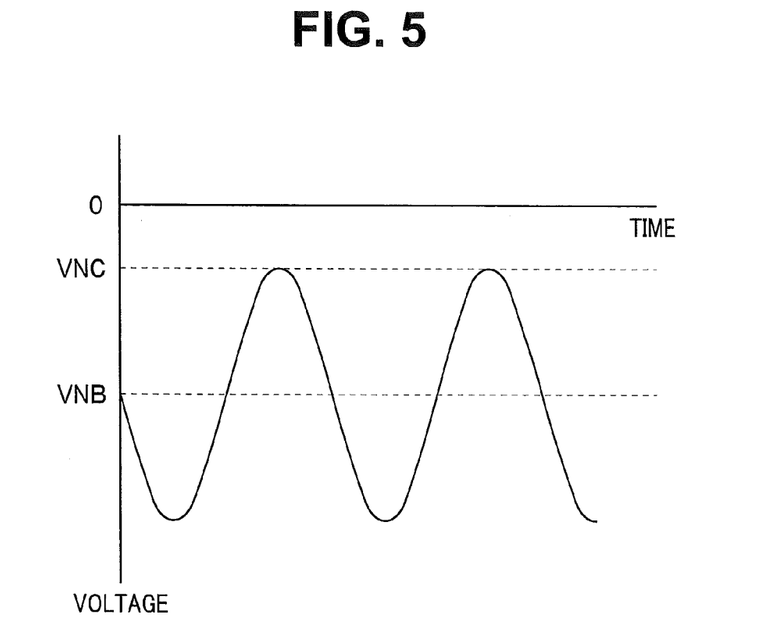
FIG. 5 is a diagram showing another example of the first drive signal used for driving the actuator unit provided in the scanning endoscope, which is different from the example of FIG. 3.
Figure 6:
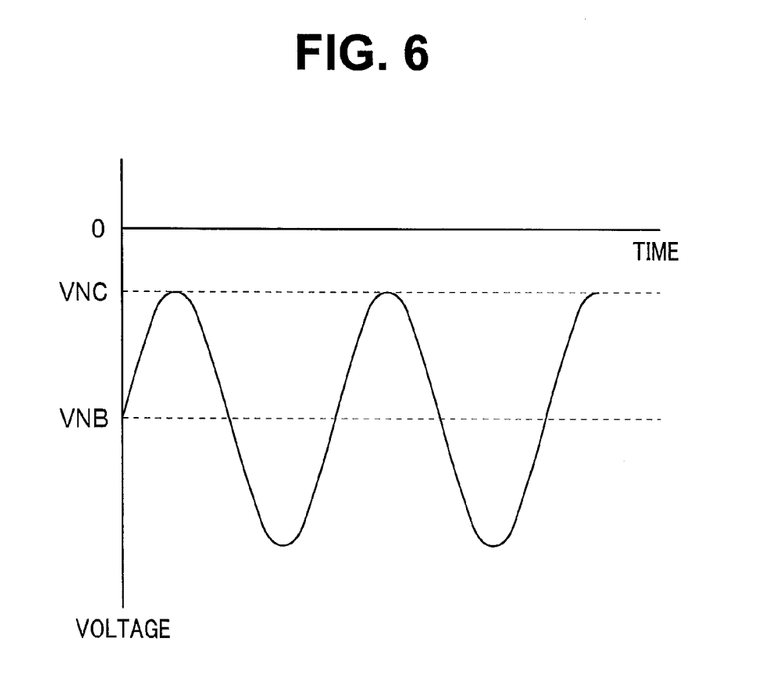
FIG. 6 is a diagram showing another example of the second drive signal used for driving the actuator unit provided in the scanning endoscope, which is different from the example of FIG. 4.

Besides, it may be configured that, by appropriately modifying the configuration of the embodiment as described above, a first drive signal having a waveform and a phase as show in FIG. 5, for example, is outputted to the actuators 15a and 15b, instead of the first drive signal having the waveform and the phase as show in FIG. 3, and a second drive signal having a waveform and a phase as shown in FIG. 6 is outputted to the actuators 15c and 15d, instead of the second drive signal having the waveform and the phase as show in FIG. 4. An operation, etc. of the case having such a configuration will be described below while omitting the substance as already described.

The signal generator 33 generates a first drive signal having a waveform and a phase as shown in FIG. 5, for example, as a drive signal for driving the actuator 15a and 15b on the basis of the control of the controller 25, and outputs the generated signal to the D/A converter 34a. FIG. 5 is a diagram showing an example of the first drive signal used in driving the actuator unit provided in the scanning endoscope, which is different from the example of FIG. 3.

Specifically, the signal generator 33 generates and outputs a first drive signal having a waveform such that a voltage value varies periodically with a voltage value VNB, which is a negative value, as a center and a maximum value VNC of the voltage value is not more than "0", and having an inverse phase with respect to a phase of a second signal of FIG. 6 (as described below) on the basis of control of the controller 25 (see FIG. 5).

Further, the signal generator 33 generates a second drive signal having a waveform and a phase as shown in FIG. 6, for example, as a drive signal for driving the actuator 15c and 15d on the basis of the control of the controller 25, and outputs the generated signal to the D/A converter 34b. FIG. 6 is a diagram showing an example of the second drive signal used in driving the actuator unit provided in the scanning endoscope, which is different from the example of FIG. 4.

Specifically, the signal generator 33 generates and outputs the second drive signal having the same waveform as the first drive signal of FIG. 5 (in which the voltage value varies periodically with the negative voltage value VNB as the center and the maximum value VNC of the voltage value is not more than "0"), and having an inverse phase with respect to the phase of the first signal of FIG. 5, on the basis of control of the controller 25 (see FIG. 6).

It is noted that the above-mentioned voltage value VNB may be a fixed value which is set in advance or a variable value which is changeable in accordance with an operation of the input device 5 as long as the value VNB is the same in the first drive signal and the second drive signal and the maximum value VNC of the voltage value is not more than "0".

On the other hand, the first drive signal of FIG. 5 generated by the signal generator 33 is outputted to the actuators 15a and 15b through the D/A converters 34a and the amplifier 35. Further, the second drive signal of FIG. 6 generated by the signal generator 33 is outputted to the actuators 15c and 15d through the D/A converter 34b and the amplifier 35.

Then, when an AC voltage in accordance with the first drive signal having the waveform and the phase shown in FIG. 5 is applied to the actuator unit 15 (the actuators 15a and 15b), an electric field is generated in the reverse direction (the positive direction of the X-axis) with respect to the polarization direction of the piezoelectric device constituting the actuator 15a, and an electric field is generated in the reverse direction (the positive direction of the Y-axis) with respect to the polarization direction of the piezoelectric device constituting the actuator 15b. Further, when an AC voltage in accordance with the second drive signal having the waveform and the phase shown in FIG. 6 is applied to the actuator unit 15 (the actuators 15c and 15d), an electric field is generated in the reverse direction (the negative direction of the X-axis) with respect to the polarization direction of the piezoelectric device constituting the actuator 15c, and an electric field is generated in the reverse direction (the negative direction of the Y-axis) with respect to the polarization direction of the piezoelectric device constituting the actuator 15d.

That is, the AC voltage in accordance with the first drive signal having the waveform and the phase shown in FIG. 5 is applied to the actuators 15a and 15b, and the AC voltage in accordance with the second signal having the waveform and the phase shown in FIG. 6 is applied to the actuators 15a and 15b, and thereby forces exerted to the ferrule 41 in accordance with the driving of the actuators 15a-15d can be balanced.

Incidentally, in a case where the illumination fiber 12 is swung according to a conventional method in which an AC voltage in accordance with a drive signal having positive and negative amplitudes with a voltage value "0" as a center is applied to the actuators 15a-15d, there arises necessity of configuring the main body apparatus 3 using an amplifier that amplifies both of a positive amplitude and a negative amplitude (as the amplifier 35) and is relatively expensive.

In contrast, according to the present modified example, since the AC voltages in accordance with the drive signals each having the waveform such that the voltage value varies periodically with the negative voltage value VNB as the center and the maximum value VNC of the voltage value is not more than "0" are applied to the actuators 15a-15d, the main body apparatus 3 can be configured using an amplifier that amplifies only an amplitude of a negative value which has relatively inexpensive (as the amplifier 35). As a result, according to the present modified example, it is possible to perform scanning of an object by the configuration of a relatively low cost in comparison with a conventional scanning endoscope system while maintaining the same function as the conventional system.

It is noted that the present invention is not limited to the above-described embodiment and modified example, and it is a matter of course that various modifications and applications can be possible in a range not to deviate from a gist of the invention.

What is claimed is:

1. A scanning endoscope system comprising:
a fiber that conducts illumination light emitted from a light source;
a first actuator that is provided laterally of the fiber, and expands and contracts in accordance with an applied voltage so as to swing the fiber;
a second actuator that is arranged at a position opposite to the first actuator with the fiber intervened in between, and expands and contracts in accordance with an applied voltage so as to swing the fiber; and
a drive-signal output section configured to output, to the first actuator, a first drive signal having either a first waveform such that a minimum value of a voltage value, which varies periodically with a first voltage value of a positive value as a center, is not less than zero, or a second waveform such that a maximum value of a voltage value, which varies periodically with a second voltage value of a negative value as a center, is not more than zero, and configured to output, to the second actuator, a second drive signal having the same waveform as the first drive signal and having a phase different from a phase of the first drive signal,
wherein the first actuator and the second actuator are formed by piezoelectric devices which are subjected to polarizing processing so that polarization directions are opposite to each other, and
wherein the first actuator generates an electric field in a forward direction with respect to the polarization direction of the piezoelectric device forming the first actuator when an AC voltage in accordance with the first drive signal having the first waveform is applied to the first actuator, and the second actuator generates an electric field in a forward direction with respect to the polarization direction of the piezoelectric device forming the second actuator when an AC voltage in accordance with the second drive signal having the first waveform is applied to the second actuator.

2. A scanning endoscope system comprising:
a fiber that conducts illumination light emitted from a light source;
a first actuator that is provided laterally of the fiber, and expands and contracts in accordance with an applied voltage so as to swing the fiber;
a second actuator that is arranged at a position opposite to the first actuator with the fiber intervened in between, and expands and contracts in accordance with an applied voltage so as to swing the fiber; and
a drive-signal output section configured to output, to the first actuator, a first drive signal having either a first waveform such that a minimum value of a voltage value, which varies periodically with a first voltage value of a positive value as a center, is not less than zero, or a second waveform such that a maximum value of a voltage value, which varies periodically with a second voltage value of a negative value as a center, is not more than zero, and configured to output, to the second actuator, a second drive signal having the same waveform as the first drive signal and having a phase different from a phase of the first drive signal,
wherein the first actuator and the second actuator are formed by piezoelectric devices which are subjected to polarizing processing so that polarization directions are opposite to each other, and
wherein the first actuator generates an electric field in a reverse direction with respect to the polarization direction of the piezoelectric device forming the first actuator when an AC voltage in accordance with the first drive signal having the second waveform is applied to the first actuator, and the second actuator generates an electric field in a reverse direction with respect to the polarization direction of the piezoelectric device forming the second actuator when an AC voltage in accordance with the second drive signal having the second waveform is applied to the second actuator.

3. The scanning endoscope system according to claim 1, wherein the second drive signal has the phase inverse to the phase of the first drive signal.

4. The scanning endoscope system according to claim 1, wherein the first voltage value is a variable value which is changeable in accordance with an operation of an input section.

5. The scanning endoscope system according to claim 1, wherein the second voltage value is a variable value which is changeable in accordance with an operation of an input section.

6. The scanning endoscope system according to claim 1, further comprising:
- a light receiving section that receives return light of the illumination light emitted to an object;
- a light detecting section configured to generate and output a signal according to intensity of the return light received by the light receiving section; and
- an image generation section configured to generate an image of the object based on the signal outputted from the light detecting section.

7. The scanning endoscope system according to claim 2, wherein the second drive signal has the phase inverse to the phase of the first drive signal.

8. The scanning endoscope system according to claim 2, wherein the first voltage value is a variable value which is changeable in accordance with an operation of an input section.

9. The scanning endoscope system according to claim 2, wherein the second voltage value is a variable value which is changeable in accordance with an operation of an input section.

10. The scanning endoscope system according to claim 2, further comprising:
- a light receiving section that receives return light of the illumination light emitted to an object;
- a light detecting section configured to generate and output a signal according to intensity of the return light received by the light receiving section; and
- an image generation section configured to generate an image of the object based on the signal outputted from the light detecting section.

\* \* \* \* \*